United States Patent [19]

Byerley et al.

[11] Patent Number: 5,453,530

[45] Date of Patent: Sep. 26, 1995

[54] S-(ω-HYDROXYALKYL) ESTERS OF THIOACRYLIC AND THIOMETHACRYLIC ACIDS

[75] Inventors: Thomas J. Byerley, Mission; Cecil C. Chappelow, Leawood; J. David Eick, Overland Park, all of Kans.

[73] Assignees: The Curators of the University of Missouri, Columbia; Midwest Research Institute, Kansas City, both of Mo.

[21] Appl. No.: 212,518

[22] Filed: Mar. 11, 1994

[51] Int. Cl.$^6$ .................................................. C07C 327/28
[52] U.S. Cl. ................................................................ 558/52
[58] Field of Search ................................................ 558/252

[56] References Cited

U.S. PATENT DOCUMENTS

| | | | |
|---|---|---|---|
| 2,454,568 | 11/1948 | Pollack | 558/252 |
| 3,022,151 | 2/1962 | Searle | 558/252 X |
| 4,397,862 | 8/1983 | Mroszczak et al. | 558/252 X |

FOREIGN PATENT DOCUMENTS

| | | | |
|---|---|---|---|
| 0165670 | 12/1985 | European Pat. Off. | 558/252 |

OTHER PUBLICATIONS

Gabriel P. Lopez et al., "plasma Deposition of Ultrathin Films of Poly(2–hydroxyethyl methacrylate): Surface Analysis and Protein Absorption Measurements", *Macromolecules*, vol. 26, No. 13 (1993).

C. S. Marvel et al., "Alkyl Thiolacrylates: Their Preparation and Polymerization", *Journal of Polymer Science*, vol. XIX, pp. 59–72 (1956).

George Braude, "Thiocarboxylic Esters and Related Compounds", *Journal Organic Chemistry*, vol. 22, pp. 1675–1678 (1957).

Gene Sumrell et al., "Preparation of Thiomethacrylate Ester. A Study of the Reaction of Sodium Mercaptides with Methacrylyl Chloride", *Journal of American Chemical Society*, vol. 80, pp. 2509–2513 (1958).

Takayuki Otsu et al., "Effect of Ester Alkyl Groups on the Co–polymerization of Alkyl Thiolacrylates with Styrene", *Die Makromolekulare Chemie*, vol. 119, pp. 140–146 (1968).

Hydrogels, Encyclopedia of Polymer Science and Engineering vol. 7, pp. 783–788 and 801–802 (1990).

*Primary Examiner*—Robert Gerstl
*Assistant Examiner*—Michael G. Ambrose
*Attorney, Agent, or Firm*—Shook, Hardy & Bacon

[57] ABSTRACT

Compounds are described which are S-(ω-hydroxyalkyl) esters of thioacrylic and thiomethacrylic acids. The compounds have the formula:

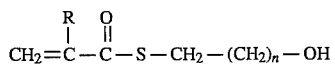

wherein:

R is hydrogen or methyl; and n is 1, 2 or 3.

These compounds can be used as conditioners to enhance the wettability of dentinal surfaces, can be employed as chemical tracers to characterize the wetting of dentinal surfaces, and can be copolymerized in situ to form potential dentinal bonding systems. The compounds can also be homopolymerized and copolymerized to form other useful products.

5 Claims, No Drawings

S-(ω-HYDROXYALKYL) ESTERS OF THIOACRYLIC AND THIOMETHACRYLIC ACIDS

BACKGROUND OF THE INVENTION

The government has certain rights in this invention pursuant to Research Grant No. NIDR DE 09696.

This invention relates in general to compositions of matter and, more particularly, to thiomethacrylic and thioacrylic acid ester compounds, methods of preparation of such compounds and polymers made therefrom.

Dental composites are typically applied in a multi-step process designed to provide a secure adhesive bond and seal at the interface of the dental adhesive and tooth surface. As an example, when the restorative is a cavity filling, the decayed tooth material is cut away and an etching composition such as citric acid is applied to the tooth surface. The etching composition serves to remove debris remaining from the cutting process and causes demineralization of a thin layer of underlying dentin to facilitate the wetting and penetration of the subsequently applied dental adhesive. A conditioner such as 2-hydroxyethylmethacrylate (HEMA) is also commonly applied to the dentin prior to or concurrently with application of the dental adhesive to enhance the wetting, penetration and bonding of the dental adhesive to the dentin.

The dental adhesive must be capable of wetting the prepared dentin surface as well as bonding with the organic composite resin which is commonly used to fill the hollow area in the portion of the tooth that has been cut away. The dental adhesive must also possess a sufficient shear bond strength to withstand the shrinkage experienced by many dental composite resins, such as those based on bis-GMA (2,2'-bis[4-(2-hydroxy-3-methacryloyloxypropoxy)]phenyl propane). The adhesive is typically a vinyl monomer mixture which undergoes chemical or photo-initiated polymerization. The composite resin may include the same or different monomer material as used for the dental adhesive, as well as suitable filler material.

HEMA homopolymers and copolymers have also been used extensively as biomaterials in diagnostic and therapeutic devices and for implants. These polymer materials are known as hydrogels because of their hydrophilicity and insolubility in water. The high water content, soft and rubbery consistency and low interfacial tension of HEMA polymers closely resemble those same properties found in living tissues. Because of these similarities, HEMA polymers have been used as diagnostic devices such as catheters, electrode catheters, carriers for enzyme immunoassay, gel-entrapped enzyme electrode probes, cell culture substrates, and electrophoresis gels. HEMA polymers have also been used in therapeutic applications as absorbent coatings for blood perfusion, hemodialysis membranes, blood oxygenators, degradable therapeutic systems, drug-delivery systems, and medicated and soft contact lenses. Implant uses of HEMA polymers includes intraocular lenses, artificial corneas, soft tissue substitutes, burn dressings, transdermal drug-delivery patches. Other uses are known, including as separation membranes.

Despite these widely varying uses of HEMA polymers, it would be desirable in certain applications to achieve a faster rate of vinyl polymerization of the HEMA monomer. Another problem presented by the use of HEMA as a dental restorative conditioner and in other tissue applications is the difficulty in determining the degree of penetration of HEMA into the underlying dentin or tissue. Radioactive labelling procedures can be used to determine the degree of penetration of HEMA, but it would be desirable to use alternate procedures which do not require the use of radioactive markers. For example, compounds containing sulfur atoms can be localized in tissue samples using energy-dispersive spectroscopy and auger spectroscopy.

Alkyl thiolacrylates are known and methods of preparation have been reported. Although alkyl thiol esters have been obtained by the treatment of a mercaptan with an acid chloride, the use of acryloyl chloride in this process has been generally unsuitable because the mercaptan is added to the carbon-carbon double bond at the same time as the formation of the ester. Instead of directly forming the thiol esters, Marvel et al. in *Journal of Polymer Science*, Vol. XIX, pages 59–71 (1956), described the process of preparing saturated alkyl thioesters by first reacting mercaptan with α,β-dibromopropionyl chloride to form the thiol ester, followed by the elimination of the bromine atoms by the addition of sodium iodide.

Braude, in *J. Organic Chem.*, Vol. 22, pages 1675–78 (1957), reported that the thioesters could be prepared by contacting methacryloyl chloride with the lead salt of the mercaptan. Sumrell et al. later disclosed that methacryloyl chloride could be directly reacted with methyl mercaptan in the presence of sodium hydroxide at a temperature below 10° C. to form methyl thiolmethacrylate. *J. Amer. Chem. Soc.*, Vol. 80, pages 2509–13 (1958). Otsu et al. have also reported on the copolymerization of several alkyl thioacrylates with styrene in *Die Makromolekulare Chemie*, Vol. 119, pages 140–146 (1968).

SUMMARY OF THE INVENTION

It is an object of this invention to provide a compound which has properties comparable to HEMA but contains a thiol group which can be localized using energy-dispersive spectroscopy so that the degree of wetting and penetration of the compound into the substrate to which it is applied can be determined without the use of radioactive labelling procedures.

It is also an object of this invention to provide a compound which can be polymerized to form homopolymer or copolymer materials for use in a wide variety of biomaterial applications.

As a corollary to the preceding object, it is another object of this invention to provide a compound which has a faster rate of vinyl polymerization in comparison to HEMA so that the compound can be used in place of HEMA, including in those applications where the faster rate of polymerization is more suitable.

In one aspect, the invention provides novel compounds of the general formula I:

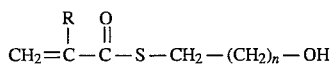

wherein:

R is hydrogen or methyl; and n is 1, 2 or 3.

In another aspect, the invention is directed to a method of preparing compounds of formula I, said method comprising serially carrying out the following steps:

(a) contacting an ω-mercaptoalkanol with an oxy-blocking agent to prepare an oxy-blocked-ω-mercaptoalkanol;

(b) contacting the oxy-blocked-ω-mercaptoalkanol with a suitable metallic substance to prepare a metallic mercaptide-salt of the oxy-blocked-ω-mercaptoalkanol;

(c) contacting the metallic mercaptide-salt of the oxy-blocked-ω-mercaptoalkanol with an acryloyl or methacryloyl halide or pseudo halide to prepare an oxy-blocked-S-(ω-hydroxyalkyl) ester of a thioacrylic or thiomethacrylic type acid; and (d) contacting the oxy-blocked-S-(ω-hydroxyalkyl) ester of a thioacrylic or thiomethacrylic type acid with a suitable deprotecting agent to prepare the S-(ω-hydroxyalkyl) ester of a thioacrylic or thiomethacrylic type acid.

The invention is also directed to homopolymers and copolymers which comprise a polymer containing a residue of a compound of the foregoing formula I and/or which have a repeating unit of the following general formula:

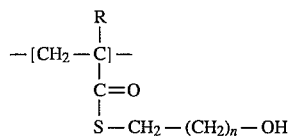

wherein R and n are as defined above.

In another aspect, the invention is directed to compounds of the general formulas II and III:

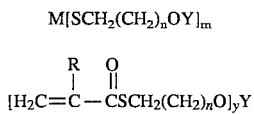

wherein:

R and n are as defined above;

M is a metal residue having a valence of m;

m is generally from 1 to 4;

Y is an oxy-blocking agent residue; and y is the valence of Y, often equal to m, e.g., 1 or 2. The compounds of formulas II and III are useful intermediates in the preparation of compounds of formula I.

DESCRIPTION OF THE PREFERRED EMBODIMENT(S)

The invention is directed, in part, to S-(ω-hydroxyalkyl) esters of thioacrylic and thiomethacrylic acids of the general formula I:

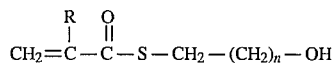

wherein:

R is hydrogen or methyl; and n is 1, 2 or 3.

Preferred compounds of formula I are those in which R is methyl or hydrogen and n is 1 or 2. More preferred are compounds in which R is methyl or hydrogen and n is 1.

Compounds encompassed within formula I include S-(2hydroxyethyl) thiomethacrylate, S-(2-hydroxyethyl) thioacrylate, S-(3-hydroxy-n-propyl) thiomethacrylate, S-(3-hydroxy-n-propyl) thioacrylate, S-(4-hydroxy-n-butyl) thiomethacrylate, and S-(4-hydroxy-n-butyl) thioacrylate. Particularly preferred are S-(2hydroxyethyl) thiomethacrylate and S-(2-hydroxyethyl) thioacrylate.

Unless specifically indicated to the contrary, to the extent the compounds of the invention may exist as optical or geometric isomers, all isomers and racemic mixtures are understood to be included in the invention. In addition, all possible isomeric forms of the compounds of the invention are within the ambit of this invention.

The invention is also directed to compounds of the general formulas II and III:

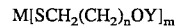

wherein:

R is hydrogen or methyl;

n is 1, 2 or 3;

M is a metal residue having a valence of m;

m is generally from 1 to 4;

Y is an oxy-blocking agent residue; and y is the valence of Y, often equal to m, e.g., 1 or 2.

Compounds of formulas II and III are useful intermediates in the preparation of the compounds of formula I. The metal residue in these intermediate compounds may be from any suitable metal. For instance, it may be of lithium or lead. Preferably, the metal residue is Pb(II). The metal may be introduced, for example, into an oxy-blocked mercaptoalkanol precursor, by employing a suitable substance (e.g., in general, MX, preferably M(X)$_y$ where M and y are as defined above and X is a suitable counterion, both present in suitable valence-balanced form). Preferred counterions are acetates.

The oxy-blocking agent (which may be represented by the formula YR', where Y is as defined above and R' comprises a group or part to complete the agent) is a substance which derivatives the required hydroxyl moiety of the S-(ω-hydroxyalkyl) thioacrylate and thiomethacrylate compound of the general formula I. This agent replaces the active hydrogen of the noted hydroxyl moiety and generally can be removed later on as by substitution of another hydro moiety for the oxy-blocking agent. Preferably, the oxy-blocking agent is a silicon-containing blocking agent, which may include so-called silane blocking, or silylating, agents. Some of the more prominent silylating agents include trimethylchlorosilane, hexamethyldisilazane, trimethylsilylamides, trimethylsilylureas, trimethylsilylamines, trimethylsilyl sulfates, t-butyldimethyl chlorosilane, t-butyldiphenylchlorosilane, and triisopropyl chlorosilane. General use of these particular agents is known in the art. Of the foregoing, hexamethyldisilazane and trimethylchlorosilane, the latter typically employed with a proton acceptor such as pyridine or triethylamine, are preferred.

Removal of the silicon-containing blocking agent can be carried out by employment of a suitable deprotecting agent (HR", wherein R" comprises a group or part to complete the agent which contains a donarable hydro moiety (H)). The deprotecting agent is a substance which can remove the residue of the silicon-containing blocking agent and substitute a hydrogen back onto the protected oxy (—O—) moiety, for example, by acidic or basic hydrolysis employing a suitable alcohol such as, for example, methanol, ethanol, propanols, and so forth and the like.

In general, conditions are those sufficient to carry out the pertinent step or process. Specific conditions can vary depending upon specific reagents employed and effects desired.

The following general reaction scheme can be employed to prepare compounds of the present invention:

Step 1:

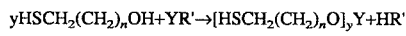

Step 2:

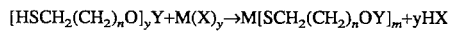

Step 3:

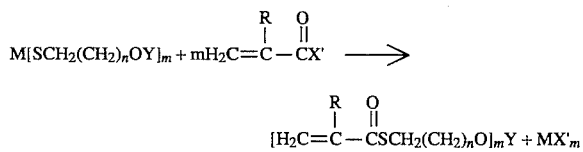

Step 4:

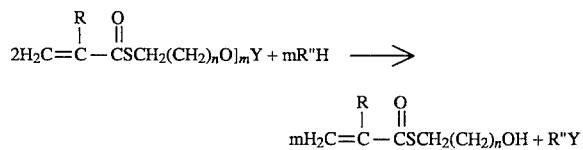

wherein:

R, Y, R', R", M, y, m and n are as set forth above; and X' is Cl, Br, I and the like.

Compounds of the present invention can be prepared in accordance with the following more detailed reaction scheme:

Step 1:

2HSCH$_2$(CH$_2$)$_n$OH+[(CH$_3$)$_3$Si]$_2$NH→2HSCH$_2$(CH$_2$)$_n$ OSi(CH$_3$)$_3$+ NH$_3$

Step 2:

2(2HSCH$_2$(CH$_2$)$_n$OSi(CH$_3$)$_3$)+Pb(OOCCH$_3$)$_2$→Pb[SCH$_2$(CH$_2$)$_n$OSi(CH$_3$)$_3$]$_2$+2CH$_3$COOH

Step 3:

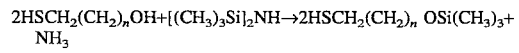

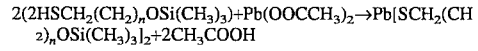

Step 4:

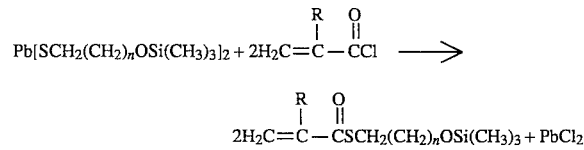

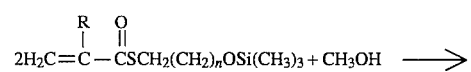

wherein R and n are as set forth above.

As a specific example, when R is methyl and n is 1, the reaction scheme can be carried out in the following manner. In step 1, 2-mercaptoethanol is treated with hexamethyldisilazane to silylate the hydroxy group to protect it from reacting with the acid chloride in subsequent reaction steps. The mercapto group does not react with the silylating reagent. In step 2, the reaction product from step 1, (2-mercaptoethoxy)trimethylsilane is reacted with lead (II) acetate which was been slurried in an inert solvent. The reaction product is the lead salt of the O-silylated mercaptoethanol. In step 3, the lead salt suspended in diethyl ether is reacted with methacryloyl chloride to form O-silylated methacrylol thiol ester and insoluble lead chloride which is removed by filtration. In step 4, methyl alcohol is added to the filtrate to hydrolyze the trimethylsilyl group from the reaction product of step 3. After removal of the solvent, a stabilizer, such as methoxyhydroquinone, is added to the residue to inhibit polymerization. The residue is subjected to fractional distillation at low pressure (0.01 mm Hg) to remove the methoxytrimethylsilane by-product. The final product, S-(2-hydroxyethyl) thiomethacrylate, is obtained as a clear mobile fluid in an overall yield of 70%.

Variations in the reactants and conditions can, of course, be employed. For example, in step 1, a mixture of trimethylisilyl chloride and triethylamine can be used as the silylating agent. In step 2, anhydrous lead (II) acetate suspended in refluxing toluene can be reacted with the silylated mercaptoethanol to obtain the mercaptide; or lead (II) acetate trihydrate suspended in diethyl ether can be reacted directly with the silylated mercaptoethanol, provided the temperature is maintained at 0° C. to prevent hydrolysis of the silyl group. In step 3, metallic derivatives other than lead, such as lithium, can be employed in the reaction with methacryloyl chloride. In step 4, when hydrated lead (II) acetate has been used in step 3, the addition of methanol is not necessary for hydrolysis because the acetic acid and water (generated in step 3) are sufficient to hydrolyze the silyl group when the temperature is increased during solvent removal.

The invention is thus directed to a process to prepare an S-(ω-hydroxyalkyl) ester of a thioacrylic or thiomethacrylic type acid comprising serially carrying out, the following steps:

(a) contacting an ω-mercaptoalkanol with an oxy-blocking agent to prepare an oxy-blocked-ω-mercaptoalkanol;

(b) contacting the oxy-blocked-ω-mercaptoalkanol with a suitable metallic substance to prepare a metallic mercaptide-salt of the oxy-blocked-ω-mercaptoalkanol;

(c) contacting the metallic mercaptide-salt of the oxy-blocked-ω-mercaptoalkanol with an acryloyl or methacryloyl halide or pseudo halide to prepare an oxy-blocked-S-(ω-hydroxyalkyl) ester of a thioacrylic or thiomethacrylic type acid; and (d) contacting the oxy-blocked-S-(ω-hydroxyalkyl) ester of a thioacrylic or thiomethacrylic type acid with a suitable deprotecting agent to prepare the S-(ω-hydroxyalkyl) ester of a thioacrylic or thiomethacrylic type acid.

The ω-mercaptoalkanol is of the general formula $HSCH_2(CH_2)_nOH$ wherein n is 1, 2 or 3; the oxy-blocking agent is a silicon-containing blocking agent; the metallic substance is a salt or compound of lithium or lead; the acryloyl or methacryloyl halide or pseudo halide is a chloride; and the S-(ω-hydroxyalkyl) ester of a thioacrylic or thiomethacrylic type acid is of the following general formula $CH_2=C(R)-(C=O)-S-CH_2-(CH_2)_n-OH$ wherein R is hydrogen or methyl and n is as defined above.

The following examples present typical syntheses as described by the reaction schemes set forth above. These examples are understood to be illustrative only and are not intended to limit the scope of the invention.

EXAMPLE 1

Preparation of S-(2-hydroxyethyl) thiomethacrylate

Silylation of 2-mercaptoethanol (37 mL, 0.5 mole) was performed with chlorotrimethylsilane (65 mL of 98%, 0.5 mole) using pyridine (0.5 mole) as a hydrogen chloride acceptor in a toluene solution. The mixture was heated to reflux and the solvent removed at atmospheric pressure. After solvent removal, the crude product was vacuum distilled. Redistillation through a fractionating column gave a 54% yield of product (99+% pure via gas chromatographic analysis).

Lead (II) acetate trihydrate was slurried with toluene and heated to reflux to remove water of hydration. The theoretical amount of water was obtained.

The hard crystalline lead acetate was slurried with the silylated 2-mercaptoethanol and the mixture warmed to reflux. The yellow lead mercaptide was filtered and washed with ether. The dried salt was suspended in ether and to this mixture was added methacryloyl chloride. From this ether solution was separated a white fluid liquid. This product had no sulfur odor and polymerized quite rapidly with tributylborane oxide (TBBO) initiator. Physical properties determined on this material were: $d^{22}$, 1.1441; $N_D^{22}$ 1.4975; $M_D$ calc'd 37.43, found 37.06; solubility parameter, $\delta_j$=24.9±0.7 (calculated using the methods of Hoy, Small, and Hoftyzer-Van Krevelin).

EXAMPLE 2

Preparation of S-(2-hydroxyethyl) thiomethacrylate

The starting material, trimethylsilyl 2-mercaptoethanol, was prepared by heating 2-mercaptoethanol with hexamethyldisilazane at 100° C. for 8 hours with a slow sweep of nitrogen. The product was distilled through a four-plate Oldershaw column. The fraction boiling from 74° to 76.5° C. at water aspirator vacuum was collected. Gas chromatography of this product indicated greater than 99% purity. The yield was 83.8% of theory.

To the slurried lead (II) acetate trihydrate (76 g, 0.02 mole) in ether at ice bath temperature was added to 6.0 g, 0.04 moles of silylated 2-mercaptoethanol. The hard, white crystalline acetate was transformed to a yellow amorphous precipitate. The mixture was stirred continuously at ice bath temperature for 1 hour. To this cold, stirred mixture was added 4.18 g. 0.04 moles of methacryloyl chloride. The yellow color was destroyed and a white gelatinous lead chloride precipitate was formed. This mixture was allowed to come to ambient temperature and stirred for several hours, after which time the lead chloride was removed by filtration. To the clear filtrate was added 4-methoxyphenol as a polymerization inhibitor. The reaction mixture was passed through a 2.5 cm by 18 cm activated alumina column. The column was then washed with 150 mL of methylene chloride. The solvents were removed on a rotary evaporator to yield a crude product of 4.1 g, or 70% of theory. Gas chromatography indicated mainly one compound. Analysis of the infrared spectrum showed that the silylated protective group had been hydrolyzed by the presence of acetic acid and water in the reaction mixture. The product was free of sulfur odor.

The compounds of formula I have utility, including as hydrophilic surface conditioners in biodental applications, such as bonding dental restoratives to dentinal structures. The compounds, when applied to dentinal surfaces, wet & penetrate the surface and undergo in situ polymerization upon application of the dental adhesive and/or the composite resin. An inter-penetrating polymer network is thus formed to securely bind the resin to the dentinal structure. Notably, because of the presence of the sulfur atom in the compounds of the invention, scanning transmission electron microscopy, electron dispersive spectroscopy and auger spectroscopy can be used to localize the compounds prior to or after polymerization and determine their penetration and wetting of the tissue. The ability to localize the compounds without using radioactive labelling procedures is particularly advantageous because of the risks associated with the use of radioactive markers. The following example is illustrative of the use of the compounds in this manner.

EXAMPLE 3

Use of HETMA in Dentinal Adhesive Systems

Ten-percent solutions of S-(2-hydroxyethyl) thiomethacrylate (HETMA) in acetone were applied to etched dentinal surfaces in the testing of conventional dentinal adhesive systems which normally use HEMA as a conditioner. The HETMA penetrated and wet the demineralized dentinal layer well and was in intimate contact with the underlying dentin, as determined by scanning transmission electron microscopy and electron dispersive spectroscopy.

The invention is also directed to homopolymer and copolymer products of the S-(ω-hydroxyalkyl) esters of thioacrylic and thiomethacrylic acids of formula I. The monomers of such esters can be polymerized using any of various suitable polymerization techniques which are known in the art. In general, those polymerization techniques which are used to homopolymerize and copolymerize HEMA are suitable for use with the compounds of the present invention. In general, vinyl polymerization of the compounds of formula I proceeds at a faster rate in comparison to HEMA, making those compounds better suited for those applications requiring a faster polymerization rate than is possible with HEMA.

The homopolymers and copolymers contain a residue of a compound of formula I and/or have a repeating unit of the following general formula:

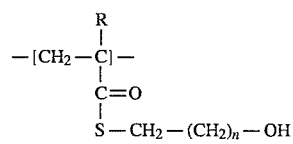

wherein R and n are as defined above.

More specifically, the homopolymers of the invention comprise a homopolymerization reaction product of a monomer of the formula:

wherein:

R is hydrogen or methyl; and n is 1, 2 or 3.

The copolymers comprise a reaction product of at least one monomer of the general formula I:

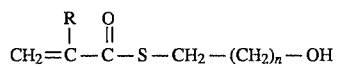

wherein:

R is hydrogen or methyl; and n is 1, 2 or 3; and at least one other monomer capable of polymerization with the monomer of the formula I.

In general, the compounds of formula I are capable of copolymerizing with those comonomers that are capable of copolymerizing with HEMA. Such comonomers are well known and include alkyl acrylates, alkyl methacrylates, hydroxyalkyl acrylates and hydroxyalkyl methacrylates among others. For example, when a crosslinked polymer capable of forming a hydrogel is desired, the comonomer can be one or more of di(ethylene glycol) diacrylate, di(ethylene glycol) dimethacrylate, tri(ethylene glycol) diacrylate, tri(ethylene glycol) dimethacrylate, tetra(ethylene glycol) diacrylate and tetra(ethylene glycol) dimethacrylate. If an optically transparent copolymer is desired, particularly suited comonomers include methylmethacrylate and ethylmethacrylate.

The compounds of formula I can also be copolymerized with ionogenic comonomers which include acids such as methacrylic, acrylic, and acrylate/methacrylate monomers containing phosphonic and sulfonic acid functionalities. An example of such a comonomer is 2-(sulfoxy) ethyl methacrylate. Other ionogenic comonomers include cationic comonomers such as 2-(N,N-diethylamino)ethyl methacrylate and 2-(N,N-dimethylamino)ethyl methacrylate. Ampholytic terpolymers such as HETMA in combination with acrylic acid, 2-(N,N-diethylamino) ethyl methacrylate or 2-(N,N-dimethylamino)ethyl methacrylate are also within the scope of the invention.

In dental applications, the compounds of formula I can be copolymerized with bis-GMA (2,2'-bis[4-(2-hydroxy-3-methacryloyloxypropoxy)]phenyl propane) and urethane dimethacrylates such as those obtained from the reaction of 1,6-hexane diisocyanate and HEMA or HETMA and the reaction of toluene 2,4'-diisocyanate and HEMA or HETMA. Reaction products of anhydrides and HEMA or HETMA, for example the reaction product of pyromellitic anhydride, trimellitic anhydride or succinic anhydride with HEMA or HETMA, can be used as a comonomer with HETMA or as a copolymer product.

The following examples illustrate methods of polymerization of the compounds of formula I.

EXAMPLE 4

Homopolymerization of S-(2-hydroxyethyl) thiomethacrylate using tri-n-butyl borane oxide as initiator Five parts of S-(2-hydroxyethyl) thiomethacrylate (HETMA), which contained about 500 ppm of 4-methoxyphenol as an inhibitor, were mixed at 25° C. with one part of tri-n-butyl borane oxide (TBBO)(AMALGAMBOND Catalyst Parkell Biomedical Division). After about 10 seconds, there was a slight exotherm and the reaction temperature rose to 27° C. The temperature was maintained at this level for 20 minutes. Then additional TBBO was added to bring the reactant/initiator ratio to 2.6 parts HETMA to 1.0 parts TBBO. The polymerization mixture reached the string point/cloud point after a total elapsed time of 30 minutes. After an additional 5 minutes, the reaction mass was an elastomeric gel. An IR spectrum of the homopolymer after 80 minutes of reaction revealed that the absorption band at 1630 $cm^{-1}$ (vinyl unsaturation) in HETMA is not present in the homopolymer.

In a second preparation, four parts of HETMA (containing about 500 ppm of methoxyhydroquinone as an inhibitor) were mixed at 39° C. with one part of TBBO. A rapid exotherm to 49° C. was noted during the first 30 seconds. The mixture was heated to 55° C. and maintained at this temperature. The string point/cloud point was reached after a total elapsed time of 7.5 minutes, and the reaction mass became an elastomeric gel after an additional 1 to 2 minutes.

EXAMPLE 5

Homopolymerization of S-(2-hydroxyethyl) thiomethacrylate using 2,2'-azobis(2-methylbutyronitrile) as initiator Twenty-five parts of HETMA (containing about 500 ppm of 4-methoxyphenol as an inhibitor) were mixed at 58° to 59° C. with one part of 2,2'-azobis(2-methylbutyronitrile) (VAZO 67, Du Pont). An exotherm to 61° C. was observed during the first 30 to 40 seconds. The temperature was maintained at 60° C. for 25 minutes. Then additional 2,2'-azobis(2-methylbutyronitrile) was added to bring the reactant/initiator ratio to 12.4 parts HETMA to 1.0 parts 2,2'-azobis(2-methylbutyronitrile). The polymerization mixture reached the string point/cloud point after a total elapsed time of 90 minutes at 60° C. After an additional 10 minutes, the reaction mass was a soft gel. The reaction mass was a stiff, elastomeric gel after a total elapsed time of 2.5 hours.

The polymers formed by the homopolymerization or copolymerization of the compounds of formula I can be used in a variety of applications, including as diagnostic devices such as catheters, electrode catheters, carriers for enzyme immunoassay, gel-entrapped enzyme electrode probes, cell culture substrates, and electrophoresis gels, therapeutic applications such as absorbent coatings for blood perfusion, hemodialysis membranes, blood oxygenators, degradable therapeutic systems, drug-delivery systems, and medicated and soft contact lenses; implants such as intraocular lenses, artificial corneas, soft tissue substitutes, burn dressings, transdermal drug-delivery patches. Other uses of the polymers can include as separation membranes. The polymers can be formed into these useful products using suitable techniques known to those of skill in the art.

From the foregoing, it will be seen that this invention is one well adapted to attain all the ends and objects herein-above set forth together with other inherent advantages.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth is to be interpreted as illustrative and not in a limiting sense.

Having thus described the invention, what is claimed is:
1. A compound of the general formula:

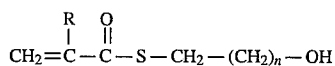

wherein:

R is hydrogen or methyl; and n is 1, 2 or 3.

2. The compound as set forth in claim 1, wherein R is hydrogen or methyl and n is 1 or 2.

3. The compound as set forth in claim 1, wherein R is methyl and n is 1.

4. The compound as set forth in claim 1, wherein the compound is S-(2-hydroxyethyl) thiomethacrylate, S-(2-hydroxyethyl) thioacrylate, S-(3-hydroxy-n-propyl) thiomethacrylate, S-(3-hydroxy-n-propyl) thioacrylate, S-(4-hydroxy-n-butyl) thiomethacrylate or S-(4-hydroxy-n-butyl) thioacrylate.

5. The compound as set forth in claim 1, wherein the compound is S-(2-hydroxyethyl) thiomethacrylate or S-(2-hydroxyethyl) thioacrylate.

* * * * *